(12) United States Patent
Kaminsky et al.

(10) Patent No.: US 7,387,981 B1
(45) Date of Patent: Jun. 17, 2008

(54) DIRECT EPOXIDATION CATALYST AND PROCESS

(75) Inventors: Mark P. Kaminsky, Media, PA (US); Roger A. Grey, West Chester, PA (US); Jay F. Miller, Chester Springs, PA (US)

(73) Assignee: Lyondell Chemical Technology, L.P., Greenville, DE (US)

(*) Notice: Subject to any disclaimer, the term of this patent is extended or adjusted under 35 U.S.C. 154(b) by 0 days.

(21) Appl. No.: 11/823,651

(22) Filed: Jun. 28, 2007

(51) Int. Cl.
*B01J 23/44* (2006.01)

(52) U.S. Cl. .................. 502/243; 502/330; 549/533

(58) Field of Classification Search .......... 502/243, 502/330; 549/533
See application file for complete search history.

(56) References Cited

U.S. PATENT DOCUMENTS

| | | | | |
|---|---|---|---|---|
| 4,410,501 | A | 10/1983 | Taramasso et al. | 423/326 |
| 4,701,428 | A | 10/1987 | Bellussi et al. | 502/8 |
| 4,764,498 | A * | 8/1988 | Wissner et al. | 502/251 |
| 4,833,260 | A | 5/1989 | Neri et al. | 549/531 |
| 4,954,325 | A | 9/1990 | Rubin et al. | 423/328 |
| 4,954,653 | A | 9/1990 | Bellussi et al. | 564/223 |
| 5,185,138 | A * | 2/1993 | Vaughan et al. | 423/710 |
| 5,500,199 | A | 3/1996 | Bellussi et al. | 423/328.2 |
| 5,623,090 | A | 4/1997 | Haruta et al. | 568/360 |
| 5,859,265 | A | 1/1999 | Müller et al. | 549/531 |
| 5,874,596 | A | 2/1999 | Onozawa et al. | 549/531 |
| 6,008,388 | A | 12/1999 | Dessau et al. | 549/531 |
| 6,077,498 | A | 6/2000 | Cabañas et al. | 423/702 |
| 6,106,803 | A | 8/2000 | Hasenzahl et al. | 423/705 |
| 6,114,551 | A | 9/2000 | Levin et al. | 549/510 |
| 6,214,958 | B1 | 4/2001 | Le-Khac et al. | 526/318.3 |
| 6,362,349 | B1 | 3/2002 | Kuperman et al. | 549/533 |
| 6,498,259 | B1 | 12/2002 | Grey et al. | 549/533 |
| 6,524,984 | B2 | 2/2003 | Carati et al. | 502/64 |
| 6,646,142 | B1 | 11/2003 | Meima et al. | 549/536 |
| 6,706,658 | B2 | 3/2004 | White | 502/182 |
| 6,815,513 | B2 | 11/2004 | Le-Khac et al. | 526/89 |
| 6,849,570 | B2 | 2/2005 | Hasenzahl et al. | 502/242 |
| 6,960,671 | B2 | 11/2005 | Cooker et al. | 549/533 |

FOREIGN PATENT DOCUMENTS

| | | |
|---|---|---|
| BE | 1001038 A7 | 6/1989 |
| EP | 0 211 985 | 8/1985 |
| JP | 4-352771 | 12/1992 |

OTHER PUBLICATIONS

R. Szostak, "Non-aluminosilicate Molecular Sieves", in *Molecular Sieves: Principles of Synthesis and Identification* (1989) Van Nostrand Reinhold, 205.
G. Vayssilov, *Catal. Rev.-Sci. Eng.*, 39(3) (1997) 209.
T. Maschmeyer et al., *Nature* 378(9) (1995) 159.
P. Tanev et al., *Nature* 368 (1994) 321.
A. Corma et al., *J. Chem. Soc., Chem. Commun.* (1998) 579.
D. Wei et al., *Catalysis Today* 51 (1999) 501.
S. Brunauer et al., *J. Am. Chem. Soc.* 60 (1938) 309.
R. Trottier et al., "Particle Size Measurement", in *Kirk-Othmer Encyclopedia of Chemical Technology*, (2007) Online Edition.
*Fundamentals of Industrial Catalytic Processes* 2nd Edition (2006), John Wiley & Sons, Inc., pp. 90-106.
C. Capes, "Particle Size Enlargement", *Handbook of Powder Technology*, 1 (1980) 112.
Y. Izumi et al., "Chapter 2 Clay as Potential Catalyst Material", *Zeolite, Clay, and Heteropoly Acid in Organic Reactions* (1992) 49, Kodansha Ltd.
T. Healy, "Stability of Aqueous Silica Sols", in *The Colloid Chemistry of Silica* (1994) 147, American Chemical Society.

* cited by examiner

*Primary Examiner*—Bernard Dentz
*Assistant Examiner*—David E Gallis
(74) *Attorney, Agent, or Firm*—Yuanzhang Han

(57) ABSTRACT

A catalyst comprising a transition metal zeolite and a supported noble metal is disclosed. The mean mass diameter of the catalyst is greater than 0.5 mm. The catalyst is formed from transition metal zeolite particles and the supported noble metal particles each having a mean mass diameter of less than 0.1 mm. An epoxidation process by reacting an olefin, hydrogen, and oxygen in the presence of the catalyst is disclosed.

20 Claims, No Drawings

DIRECT EPOXIDATION CATALYST AND PROCESS

FIELD OF THE INVENTION

The invention relates to a catalyst comprising a transition metal zeolite and a supported noble metal, and an epoxidation process comprising reacting an olefin, hydrogen, and oxygen in the presence of the catalyst.

BACKGROUND OF THE INVENTION

Direct epoxidation of higher olefins (containing 3 or more carbon atoms) such as propylene with oxygen and hydrogen has been the focus of recent efforts. For example, the reaction may be performed in the presence of a catalyst comprising gold and a titanium-containing support (see, e.g., U.S. Pat. Nos. 5,623,090, 6,362,349, and 6,646,142), or a catalyst containing palladium and a titanium zeolite (see, e.g., JP 4-352771).

Mixed catalyst systems for olefin epoxidation with hydrogen and oxygen have also been disclosed. For example, Example 13 of JP 4-352771 describes the use of a mixture of titanosilicate and Pd-on-carbon for propylene epoxidation. U.S. Pat. No. 6,008,388 describes a catalyst comprising a noble metal and a titanium or vanadium zeolite, but additionally teaches that the Pd can be incorporated into a support before mixing with the zeolite. The catalyst supports disclosed include silica, alumina, and activated carbon. U.S. Pat. No. 6,498,259 discloses the epoxidation of an olefin with hydrogen and oxygen in a solvent containing a buffer in the presence of a catalyst mixture containing a titanium zeolite and a noble metal catalyst. It is postulated that hydrogen peroxide, which is formed by reacting hydrogen and oxygen over the noble metal catalyst, reacts with the olefin in the presence of the titanium zeolite to form epoxide.

The direct epoxidation may be performed in a slurry or a fixed bed (see, e.g., U.S. Pat. No. 6,498,259). In a slurry process, catalyst particles of <100 μm are typically used; the separation of liquid product stream from catalyst particles by, e.g., filtration, is often troublesome. It is desirable, particularly in a fixed-bed process, to use catalysts of larger particle size, e.g., >0.5 mm, for the ease of separation and acceptable pressure drop across the bed.

Mixed catalyst systems have been used for other reactions. EP 0 211 985 discloses a process using a mixture of an olefin disproportionation catalyst and a double bond isomerization catalyst. Examples II and III of EP 0 211 985 illustrate that mixtures of the two catalysts with particles of 0.42 mm to 0.84 mm in diameter (20 to 40 mesh) give good activities.

SUMMARY OF THE INVENTION

The invention is a catalyst comprising a transition metal zeolite and a noble metal. The mean mass diameter of the catalyst is greater than 0.5 mm. The catalyst is formed from transition metal zeolite particles and supported noble metal particles each having a mean mass diameter of less than 0.1 mm. The catalyst is used for the production of an epoxide by reacting with an olefin, hydrogen, and oxygen. The reaction mixture can be easily separated from the catalyst. The catalyst is particularly useful in a continuous fixed-bed epoxidation process.

DETAILED DESCRIPTION OF THE INVENTION

In one aspect, the invention is a catalyst comprising a transition metal zeolite and a supported noble metal. Zeolites are porous crystalline solids with well-defined structures. Generally they contain one or more of Si, Ge, Al, B, P, or the like, in addition to oxygen. Many zeolites occur naturally as minerals, and are extensively mined in many parts of the world. Others are synthetic, and are made commercially for specific uses. Zeolites have the ability to act as catalysts for chemical reactions which take place mostly within the internal cavities of the zeolites. Transition metal zeolites are zeolites comprising transition metals in framework. A transition metal is a Group 3-12 element. The first row of transition metals includes elements from Sc to Zn. Preferred transition metals are Ti, V, Mn, Fe, Co, Cr, Zr, Nb, Mo, and W. More preferred are Ti, V, Mo, and W. Most preferred is Ti.

Preferred titanium zeolites are titanium silicates (titanosilicates). Preferably, they contain no element other than titanium, silicon, and oxygen in the lattice framework (see R. Szostak, "Non-aluminosilicate Molecular Sieves," in *Molecular Sieves Principles of Synthesis and Identification* (1989), Van Nostrand Reinhold, pp. 205-282). Small amounts of impurities, e.g., boron, iron, aluminum, phosphorous, copper, and the like, and mixtures thereof, may be present in the lattice. The amount of impurities is preferably less than 0.5 wt. %, more preferably less than 0.1 wt. %. Preferred titanium silicates generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). Particularly preferred titanium zeolites are titanium silicalites (see *Catal. Rev.-Sci. Eng.*, 39(3) (1997) 209). Examples of these include TS-1 (titanium silicalite-1, a titanium silicalite having an MFI topology analogous to that of the ZSM-5 aluminosilicate), TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, ZSM-12, MCM-22, MCM-41, and MCM-48 are also suitable for use. Examples of MCM-22, MCM-41, and MCM-48 zeolites are described in U.S. Pat. Nos. 4,954,325, 6,077,498, and 6,114,551; Maschmeyer, T., et al, *Nature* 378(9) (1995) 159; Tanev, P. T., et al., *Nature* 368 (1994) 321; Corma, A., *J. Chem. Soc., Chem. Commun.* (1998) 579; Wei D., et al., *Catalysis Today* 51 (1999) 501). The most preferred is TS-1.

A transition metal zeolite is generally prepared in the presence of an organic templating agent (see, e.g., U.S. Pat. No. 6,849,570). Suitable templating agents include alkyl amines, quaternary ammonium compounds, etc. When a zeolite is crystallized, it usually contains organic templating agent within its pores. Zeolites containing templating agents may be used to prepare the catalyst of invention without being calcined. Alternatively, a zeolite is calcined in an oxygen-containing atmosphere to remove the templating agent before it is used to prepare the catalyst of the invention.

Transition metal zeolite particles include transition metal zeolite crystals (including crystal aggregates, see, e.g., U.S. Pat. No. 5,874,596 and U.S. Pat. Appl. No. 20040059139) and formed particles (e.g., granules, pellets, and the like) containing a transition metal zeolite. A spray-dried transition metal zeolite containing a binder (silica, alumina, titania, and the like) may be used (see, e.g., U.S. Pat. Nos. 4,954,653, 4,701,428, 5,500,199, 6,524,984, and 6,106,803).

The catalyst comprises a supported noble metal. Suitable noble metals include, e.g., gold, silver, platinum, palladium, iridium, ruthenium, rhenium, rhodium, osmium, and mixtures thereof. Palladium, gold, and palladium-gold mixtures are particularly desirable.

The supported noble metal comprises a carrier. Any inorganic carrier may be used, e.g., silicas, aluminas, titanias, zirconias, magnesias, silica-aluminas silica-titanias, zeolites, clays, diatomaceous earths, and the like, and mixtures thereof. Preferred carriers include silicas, aluminas, titanias, and mixtures thereof. Titanias are particularly preferred. Preferred carriers have a BET surface area of from 5 to 1000 $m^2/g$ (see S. Brunauer, P. H. Emmett and E. Teller, *J. Am. Chem. Soc.* 60 (1938) 309). The manner in which the noble metal is incorporated into the carrier is not critical. For example, the noble metal may be supported on the carrier by impregnation, ion exchange, adsorption, precipitation, or the like.

There are no particular restrictions regarding the choice of the noble metal compound or complex used as the source of the noble metal for the preparation of the supported noble metal. Suitable compounds include nitrates, sulfates, halides (e.g., $Na_2PdCl_4$, $NaAuCl_4$), carboxylates (e.g., acetate), and amine or phosphine complexes of noble metals (e.g., palladium(II) tetraammine bromide, tetrakis(triphenylphosphine) palladium).

The weight ratio of the transition metal zeolite to the noble metal contained in the catalyst is not particularly critical. However, a transition metal zeolite to noble metal ratio of 10:1 to 5000:1 (grams of transition metal zeolite per gram of noble metal) is preferred.

The catalyst may comprise a promoter. A promoter helps to improve the catalyst performance (e.g., activity, selectivity, life of the catalyst). Preferred promoters include lead, zinc, alkaline earth metals, lanthanide metals, and the like. Lead is particularly preferred. The promoter may be added on the transition metal zeolite, the supported noble metal, or during the forming of the catalyst. While the choice of compounds used as the promoter source is not critical, suitable compounds include metal carboxylates (e.g., acetate), halides (e.g., chlorides, bromides, iodides), nitrates, sulfate, and the like. The typical amount of promoter metal present in the catalyst will be in the range of from about 0.001 to 5 wt. %, preferably 0.001 to 2 wt. % relative to the catalyst.

The catalyst has a mean mass diameter of greater than 0.5 mm. Such a catalyst is suitable for a slurry or fixed-bed process, where the catalyst may be easily separated from the reaction mixture. The mean mass diameter is the arithmetic mean diameter of all the particle masses forming the entire population (R. Trottier and S. Wood, "Particle Size Measurement," in *Kirk-Othmer Encyclopedia of Chemical Technology*, online edition, 2007).

The catalyst of the present invention is formed from distinct transition metal zeolite particles and supported noble metal particles each having a mean mass diameter of less than 0.1 mm. Preferably, they are less than 0.05 mm, more preferably less than 0.02 mm. The catalyst may be in the form of extrudates, pellets, granules, tablets, and the like. It may be produced by any suitable forming techniques, including extrusion, palletizing, tableting, and the like (*Fundamentals of Industrial Catalytic Processes* 2nd Edition (2006) John Wiley & Sons, Inc. pp. 90-106). It has been taught that an oxidation catalyst may be prepared by impregnating or reacting a transition metal zeolite with a solution of noble metal source. See, e.g. U.S. Pat. Nos. 5,859,265 and 6,008,388. In a catalyst prepared by the impregnation method, at least a portion of the noble metal is deposited on the zeolite. The present invention allows flexibilities in choosing the carrier for the noble metal. The catalyst can benefit from the interaction between the carrier and the noble metal. The catalyst may be more stable than that prepared by impregnating a transition metal zeolite with a noble metal source, due to the stronger interaction between the noble metal and the carrier.

One preferred method of forming the catalyst into particles is extrusion. Extrusion is a manufacturing process in which a material is pushed through a die or an orifice to create long objects of a fixed cross-section, which are called extrudates. Extrusion is commonly used in forming catalysts. Any conventional extruder may be used. The extrudate usually has a diameter of 0.5 to 10 mm, in particular from 0.5 to 5 mm. A suitable screw-type extruder is described in "Particle size enlargement," *Handbook of Powder Technology*, vol. 1 (1980), pp. 112-22. The catalyst may be formed by extruding a mixture comprising the transition metal zeolite and the supported noble metal.

The mixture suitable for extrusion may contain an extrusion aid. An extrusion aid helps the mixing, mulling, and extrusion, and may improve the physical properties of the extrudate such as mechanical strength, surface area, pore size, and pore volume. For example, an extrusion aid may promote the bridging of particles of the transition metal zeolite and the supported noble metal during the kneading, extruding, and drying steps and/or ensure the mechanical stability of the extrudate during extrusion and calcination. The extrusion aides are usually removed during calcination.

Suitable extrusion aids include alkyl amines, carboxylic acids, alkyl ammonium compounds, amino alcohols, cellulose, cellulose ethers, starch, polyacrylates, polymethacrylates, poly(vinyl alcohol)s, poly(vinylpyrrolidone)s, poly (amino acid)s, polyethers, poly(tetrahydrofuran)s, metal carboxylates, and the like, and mixtures thereof. Examples of cellulose ethers include sodium carboxymethylcellulose, hydroxyethylcellulose, methylcellulose, and derivatives thereof. Preferred poly(alkylene oxide)s are poly(ethylene oxide)s, poly(propylene oxide)s, or copolymers of ethylene oxide and propylene oxide (see U.S. Pat. No. 6,706,658). One particularly preferred extrusion aid is a comb-branched polymer disclosed in U.S. Pat. Nos. 6,214,958, 6,815,513, and co-pending application Ser. Nos. 11/641,317 and 11/641,482, the teachings of which are herein incorporated by reference. A comb-branched polymer comprises a polymer backbone, a carboxylic side-chain, and a polyether side-chain. The carboxylic side-chain may comprise a carboxylic acid, a carboxylate salt, or mixtures of both. The preferred carboxylic side chain is a carboxylic acid group (—COOH). The preparation of a comb-branched polymer is shown in Example 1.

The mixture suitable for extrusion may contain a catalyst binder. A binder helps to improve the mechanical strength or the physical properties of the extrudate (e.g., crush strength, surface area, pore size, pore volume). Sometimes the binder can modify the chemical properties (e.g., acidity, basicity) of the active components (the transition metal zeolite and the supported noble metal) and its catalytic activity. Suitable binders include metal oxides, non-metal oxides, mixed oxides, clays, and the like. Examples of suitable binders include silicas, aluminas, titanias, zirconias, magnesias, silica-aluminas, silica-titanias, montmorillonites, kaolins, bentonites, halloysites, dickites, nacrites, and anauxites, and the like, and mixtures thereof. Examples of clays can be found in "Chapter 2. Clay as Potential Catalyst Material," *Zeolite, Clay, and Heteropoly Acid in Organic Reactions* (1992) Kodansha Ltd., Tokyo. Preferred binders are silicas, aluminas, titanias, zirconias, magnesias, silica-aluminas, silica-titanias, kaolins, and mixtures thereof. More preferred are silicas, aluminas, titanias, and mixtures thereof. Precursors of binders are often used in preparing the mixture for extrusion. For example, silica may be introduced into the mixture as a silica sol (Healy, T. W., "Stability of Aqueous Silica Sols," in *The Colloid Chemistry of Silica* (1994) American Chemical Society). Similarly, other binder precursors such as ortho-silicic esters, alkoxysilanes, alkoxytitanates, alkoxyaluminates can also be used. Specific examples are tetramethoxysilane, tetraethoxysilane, tetrapropoxysilane, tetrabutoxysilane, and analogous tetraalkoxytitanium, and trialkoxyaluminium compounds. Precursors are converted to the corresponding binder during mixing, extrusion, or calcination.

The extruded catalyst may be calcined. The calcination may be carried out in an inert atmosphere or an oxygen-containing atmosphere. Suitable temperature for calcinations is between 200 to 900° C., more preferably from 350 to 700° C.

The catalyst is optionally reduced in the presence of a hydrogen-containing gas at a temperature from about 20 to 600° C., preferably from 50 to 200° C.

In another aspect, the invention is an epoxidation process comprising reacting an olefin, hydrogen, and oxygen in a solvent in the presence of the catalyst of the present invention.

An olefin is used in the process. Suitable olefins include any olefin having at least one carbon-carbon double bond, and generally from 2 to 60 carbon atoms. Preferably the olefin is an acyclic alkene of from 2 to 30 carbon atoms; the process is particularly suitable for epoxidizing $C_2$-$C_6$ olefins. More than one double bond may be present in the olefin molecule, as in a diene or triene. The olefin may be a hydrocarbon or may contain functional groups such as halogen, carboxyl, hydroxyl, ether, carbonyl, cyano, or nitro groups, or the like. In a particularly preferred process, the olefin is propylene and the product is propylene oxide.

The process requires the use of oxygen and hydrogen. Although any sources of oxygen and hydrogen are suitable, molecular oxygen and molecular hydrogen are preferred. The molar ratio of hydrogen to oxygen can usually be varied in the range of $H_2:O_2=1:100$ to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert gas is preferably used in the process. Any desired inert gas can be used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert gases. Mixtures of inert gases can also be used. The molar ratio of olefin to inert gas is usually in the range of 100:1 to 1:10 and especially 20:1 to 1:10.

The process preferably uses a solvent. Suitable solvents are liquid under the reaction conditions. They include, for example, oxygen-containing hydrocarbons such as alcohols, aromatic and aliphatic solvents such as toluene and hexane, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, tert-butanol, and mixtures thereof. Fluorinated alcohols can be used.

The process may be performed in a slurry or fixed-bed process. The fixed-bed process is preferred. The process is carried out at a temperature effective to achieve the desired olefin epoxidation, preferably at temperatures in the range of 0-200° C., more preferably, 20-150° C. It is advantageous to work at a pressure of 1-200 bars.

It may be advantageous to use a buffer. The buffer is employed in the reaction to inhibit the formation of glycols or glycol ethers during the epoxidation, and it can improve the reaction rate and selectivities. The buffer is typically added to the solvent to form a buffer solution, or the solvent and the buffer are added separately. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkyl-ammoniums, pyridiniums), alkyl-phosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphates, and ammonium hydroxide.

Following examples further illustrate the invention.

EXAMPLE 1

Comb-Branched Polymer (Polymer A)

The reaction is carried out in a 1-L reaction kettle equipped with a stirrer, a temperature controller, a heating device, a nitrogen purge device and a product outlet. The outlet tube is set so that the reactor holds about 320 mL of material. There are three inlet addition pumps, one for the mixture of monomers in water, one for the initiator, and one for the chain-transfer agent. The product outlet tube leads into a second reactor that is equipped with a stirrer, a temperature controller, a heating device and a nitrogen purge device. The second reactor is sized to collect all product produced after the reaction has reached steady state.

The first reactor is charged with 50 mL of water to cover the stirrer and the reactor is then purged with nitrogen for about 20 min. A mixture of a methacrylate of an oxyethylene/oxypropylene random copolymer having an oxyethylene/oxypropylene ratio of 70:30 by weight and a number average molecular weight of about 3,000 (900 g, 0.3 mol), acrylic acid (136 g, 1.83 mol), and water (610 g) is charged to the monomer feed tank. An aqueous ammonium persulfate solution (1.25 wt. %) is charged to the initiator feed reservoir and an aqueous 3-mercaptopropionic acid solution (2.2 wt. %) is charged to the chain transfer agent feed reservoir. The reactor is heated to 65° C. under a continuous nitrogen purge. The feed pumps are started with a feed rate of 150 g/h for the monomer feed, 28.5 mL/h for the initiator feed, and 30.5 mL/h for the chain transfer agent feed. The reactor effluent is diverted until the reaction has reached a steady state and then the product is collected in the second reactor for about 1 h. At the end of the period the second reactor is heated for another 3 h to complete the reaction. The product is designated as Polymer A (MW 45,000).

A sample of Polymer A is titrated with an aqueous ammonium hydroxide solution to obtain a sample designated as Polymer A-1 with pH=2.8. Polymer A-1 contains 43 wt. % solid.

EXAMPLE 2

Pd/Au-On-Titania (Catalyst B)

An aqueous $Na_2PdCl_4$ solution (19.74 wt. %, 2.77 g), an aqueous $NaAuCl_4$ solution (19.95 wt. %, 2.51 g), and DIUF water (deionized and ultrafiltered, obtained from Fisher, 250 g) are charged in a 500-mL round bottom flask. The above mixture is placed on a rotovap and mixed at 30 rpm for 0.5 h. To this solution, titania powder (DT-51A, Millennium Chemicals, mean mass diameter=1.4 μm, 100 g) is added. The pH of this solution is 3.1. Additional DIUF water (20 g) is used to rinse residual titania from the funnel into the slurry.

To this slurry, $NaHCO_3$ (15.87 g) is slowly added while it is mixed to raise the pH to 7.1. Gaseous $CO_2$ was emitted from the solution during the addition. The flask is then rotated at 30 rpm and at 40° C. for 24 h under a slow nitrogen purge. Filtering above slurry gives a dark grey powder. The powder is dried in an oven at 60° C. for 21 h under nitrogen purge, then dried at 60° C. for 6.5 h under vacuum. The dried powder is calcined in a muffle furnace in air using the following temperature program: 5° C./min ramp from 22° C. to 110° C., hold at 110° C. for 2 h, ramp 2° C./min from 110° C. to 400° C., hold at 400° C. for 8 h, cool to room temperature. The calcined powder is placed on a pressure filter with 0.22 micron filter paper and washed with DIUF water until no chloride is detected in the washing solution (Cl<1 ppm). About 1,800 mL DIUF water is used. The washed powder is dried and calcined in air as follows: 5° C./min ramp from 22° C. to 110° C., hold at 110° C. for 2 h, ramp 2° C./min from 110° C. to 550° C., hold at 550° C. for 8 h, cool to room temperature.

The calcined powder is placed in a vertical quartz tube that is heated with an electric tube furnace and is treated with a gas (5 vol. % hydrogen in nitrogen) at 100° C. for 8 h. The reduced powder turns from dark grey to black. The material obtained is designated as Catalyst B. Catalyst B contains 0.99 wt. % Pd, 0.46 wt. % Au, and 0.16 wt. % Na. Chloride level is less than 10 ppm. The nitrogen BET surface area is 64 m²/g.

EXAMPLE 3

Extrudate Containing TS-1 and Pd/Au-On-Titania (Catalyst C)

Titanium silicalite-1 (TS-1) is prepared by following procedures disclosed in U.S. Pat. Nos. 4,410,501 and 4,833,260, and calcined in air at 550° C.

TS-1 (mean mass diameter=0.2 μm, 61.1 g), Catalyst B prepared in Example 2 (6.13 g), carboxymethylcellulose sodium salt (high viscosity, Aldrich, 2.85 g), and poly(ethylene oxide) (Aldrich, 100,000 MW, 0.97 g) are mixed in a plastic beaker, then transferred to a clean dry ball mill with zirconia beads. The ball mill is sealed and rolled at 60 rpm for 1 h. The resulting mixture contains grey Pd/Au-on-titania clumps and white TS-1 powder. A metal spatula is used to break up the clumps, after which the powder is transferred to a Brabender Prep-Mixer-Muller fitted with Sigma blades which is rotating at 30 rpm for 13 min at 23° C. A sample of Polymer A-1 (17 g) is added to the mixture in the muller while the blade is rotating at 30 rpm. Then Ludox AS-40 silica sol (Aldrich, 40 wt. % silica, 39.5 g) is added to the muller. After another 5 min of mulling, DIUF water (16.5 g) is added to the muller. It is then mixed for another 8 min at 30 rpm. The resulting paste, which is homogeneously grey in color, is removed and placed in a plastic bag. The paste ages at room temperature in the bag for 3 days.

The paste is extruded with a Brabender 10:1 single screw ¾" diameter extruder fitted with a ¹⁄₁₆" single die. With the extruder turning at 10 rpm, the paste is added to the extruder. Extrudate emerges from the die. The extrudates obtained are dried at room temperature in air overnight, then dried at 63° C. for 4 h under vacuum, and calcined in a muffle furnace in air at 550° C. for 8 h (temperature ramp rate 2-5° C./min).

The extrudates are reduced at 110° C. under a gas flow (5 vol. % hydrogen in nitrogen) for 8 h in a quartz tube heated by a vertical electric tube furnace. The extrudates (Catalyst C) contains 0.08 wt. % Pd, 0.03 wt. % Au, 5.7 wt. % Ti, 0.22 wt. % Na, <100 ppm Al, <0.1 wt. % C, and <0.1 wt. % N. The nitrogen BET surface area is 320 m²/g. Its crush strength is 2.3 lbs. The crush strength is measured by using a Chatillon-Antek DFS Digital Force Gauge, fitted with flat platens on an MT test stand using an average of 10 extrudates that ranges in length from 5 to 8 mm. The DFS gauge is set in the "Break Detect" Mode which stores the maximum force (in lbs) exerted before the extrudate breaks. The force exerted for total extrudate crush is recorded as described in ASTM D 4179-01.

EXAMPLE 4

Extrudate Containing TS-1 and Pd/Au-On-Titania (Catalyst D)

Catapal D Boehmite alumina powder (Sasol, 42 g), glacial acetic acid (5.2 g), and DIUF water (80 g) is mixed for 5 min, a grey thick sol is formed. Into the sol, a mixture of TS-1 (60 g) and Catalyst B (8.1 g) is added. A thick grey paste is formed, which is transferred to the Prep-Mixer Muller with oiled Sigma blades. Carboxymethylcellulose sodium salt (5 g) and poly(ethylene oxide) (Aldrich, 100,000 MW, 1.05 g) is added to the mixer; it is then mixed at 5 rpm for 4 min and at 10 rpm for 3 min to form a paste. Into the above paste a mixture containing Catapal D alumina (16.8 g), Catalyst B (3.3 g), and TS-1 (24 g) is added. The newly formed mixture is transferred to the Prep-Mixer Muller equipped with oiled Sigma blades turning at 10 rpm. Into the muller, glacial acetic acid (2.3 g) and Polymer A-1 (10 g) are added. The muller speed is increased to 20-25 rpm. The paste obtained is stored in a plastic bag for 4 h.

The paste is extruded, dried, calcined, and reduced by following the procedure of Example 3. Catalyst D is obtained. It contains 0.07 wt. % Pd, 0.03 wt. % Au, 18 wt. % Al, 6.4 wt. % Ti, 0.24 wt. % Na, <0.1 wt. % C, and <0.1 wt. % N. The nitrogen BET surface area is 320 m²/g.

EXAMPLE 5

Extrudate Containing TS-1 and Pd/Au-On-Titania (Catalyst E)

Catalyst E is prepared in a similar fashion as Catalyst D. Catalyst E contains 0.05 wt. % Pd, 0.04 wt. % Au, 13 wt. % Al, 7.4 wt. % Ti, 0.32 wt. % Na, <0.1 wt. % C, and <0.1 wt. % N.

EXAMPLE 6

Extrudate Containing TS-1 and Pd/Au-On-Titania (Catalyst F)

Catalyst F is prepared in a similar fashion as Catalyst D. Catalyst F contains 0.06 wt. % Pd, 0.04 wt. % Au, 11 wt. % Al, 8.2 wt. % Ti, 0.45 wt. % Na, <0.1 wt. % C, and <0.1 wt. % N.

EXAMPLE 7

Pellets Containing TS-1 and Pd/Au-On-Titania (Catalyst G)

A capped glass jar containing TS-1 (24.06 g), a Pd/Au-on-titania catalyst (prepared in similar fashion as catalyst B, containing 1 wt. % Pd and 0.5 wt. % Au, 4.0 g), Catapal D Boehmite alumina (5.0 g), Sterotex K-NF organic binder (ABITEC Group, 3.0 g) is rolled at 30 rpm for 2 h to mix the powder. The mixture is further ground with a mortar and pestle. A sample of the mixture thus obtained (5 g) is placed in a hydraulic press fitted with tungsten carbide die. The powder is pressed to about 8,000-9,000 psig over a die with 1%" diameter. The pellets obtained are calcined in air by the following temperature program: from 25 to 110° C. at 5° C./min, hold at 110° C. for 2 h, ramp at 2° C./min to 550° C., hold for 10 h, cool to room temperature.

The calcined pellets are crushed to a 15-45 mesh size and are reduced at 110° C. under a gas flow (5 vol. % hydrogen in nitrogen) for 8 h in a quartz tube heated by a vertical electric tube furnace. Catalyst G contains 0.07 wt. % Pd, 0.17 wt. % Au, 35 wt. % Si, 8.6 wt. % Ti, 0.03 wt. % Na, <0.1 wt. % C, and <0.1 wt. % N.

EXAMPLE 8

Propylene Epoxidation with Catalyst C

Catalyst C (from Example 3) is tested in a Robinson-Mahoney basket reactor (available from Autoclave-Engineering) in a continuous gas flow and liquid flow mode for epoxidation of propylene.

Catalyst C (1/16" in diameter, 1/4" in lengths, mean mass diameter 1 mm, 15 g) and rutile extrudates (inert diluent, surface area 2 m²/g, 1/16" in diameter 1/4" in length) are mixed and charged into a stainless steel mesh basket (50 mL in volume). Enough rutile extrudates are used to completely fill the basket in order to minimize movement of the bed upon agitation. An agitator shaft runs through the middle of the stationary basket. The agitator typically runs at 500 to 1200 rpm to ensure proper back-mixing of gas and liquid with the catalyst. The reactor is charged with methanol/DIUF water (80/20 weight ratio, 450 mL) containing 0.008 M ammonium dihydrogen phosphate (referred to as solvent/buffer solution). The basket and agitator are attached to the reactor head which is then bolted to the reactor body. A gas feed (4.5 mol. % oxygen, 2.25 mol. % hydrogen, 86.4 mol. % nitrogen, 6.36 mol. % propylene, 0.45 mol. % methane) is then flowed through the reactor (flow rate 6670 mL/min). Electronic mass flow controllers are used for the gases and a HPLC piston type pump is used to pump the solvent/buffer solution. Dip tubes direct the gas and liquid feed flow to below the catalyst basket where they pass through metal fritted filters to break up gas bubbles upon entering the reaction solution. The reactor pressure is 500 psig. The product gas and liquid exit the reactor through fritted metal filters attached to vent lines which then go to a gas/liquid separator. The gas is then directed to an on-line gas chromatograph (GC) for analysis and the liquid is injected on both an on-line and an off-line GC. The products formed include propylene oxide (PO), propane, and derivatives of propylene oxide such as propylene glycol, propylene glycol monomethyl ethers, dipropylene glycol, and dipropylene glycol methyl ethers. Selected results are shown in Table 1. The catalyst productivity is defined as the grams of propylene oxide (PO) formed (including PO that is subsequently reacted to form PO derivatives) per gram of catalyst per hour (g POE/g Cat/h). PO and PO equivalent, POE (mole)=moles of PO+moles of PO units in the PO derivatives. PO/POE=(moles of PO)/(moles of POE)×100. Propylene to POE selectivity=(moles of POE)/(moles of propane formed+moles of POE)×100. Minimal catalyst attrition or crushing occurred during this run.

EXAMPLES 9-12

Propylene Epoxidation with Catalysts D, E, F, G

The procedure of Example 8 is repeated except Catalyst D, E, F, G is used respectively instead of Catalyst C. The amount of catalyst used and epoxidation results are shown in Table 1.

In Table 1, Catalysts C, D, E, F, and G are prepared from TS-1 crystals with a mean mass diameter of 0.2 μm and Catalyst B (supported noble metal catalyst) with a mean mass diameter of 1.4 μm. Table 1 shows that as the catalyst loading in the epoxidation reactor increases under otherwise the same reaction conditions, the catalyst productivity decreases. The results indicate that the epoxidation is diffusion controlled when the catalyst loading is high and it is chemically controlled when the catalyst loading is low. Example 8 has a catalyst loading of 15 g and it gives the highest productivity, 0.13 gram PO per gram of catalyst per hour.

COMPARATIVE EXAMPLE 13

TS-1/Silica Extrudate (Catalyst H)

TS-1 (mean mass diameter=0.2 μm, 120 g), sodium carboxymethylcellulose (5.4 g), and 1.76 g of polyethylene oxide (PEO, Aldrich, 100,000 MW, 1.76 g) are mixed with a spatula in a plastic beaker. The mixed powder is poured in a clean-dry Brabender Prep-Mixer-Muller turning at 20-30 rpm. Low Sheer Sigma Blades are installed. After it is mixed for a few minutes, a sample of Polymer A-1 (34.2 g) is poured into the muller and mixed for 5 min. Ludox A-40 silica sol (Aldrich, 40 wt. % silica, 80.4 g) is poured into the muller while it is rotating at 30 rpm. Then DIUF water (28 g) is added in 2-5 mL aliquots. The paste is further mixed for about 3 min. The white paste is removed from the muller and placed in a plastic bag for aging.

After 2 days of aging in the bag the paste is extruded using a Brabender single screw extruder run at 10 rpm with 1/16" die as described in Example 3. After the extrudates are made, they are dried in air overnight and then calcined in air with the following program: 25-110° C. at 5° C./min, hold for 3 h at 110° C., then ramp at 2° C./min to 550° C., hold for 8 h, cool to room temperature. The calcined extrudates (Catalyst H) have a crush strength of 2.7 lbs. It contains about 80 wt. % TS-1.

COMPARATIVE EXAMPLE 14

Pd/Au-Titania (Catalyst I)

Titania Extrudate Preparation. A mixture containing titania powder (Millennium Chemicals DT51, 400 g), carboxymethylcellulose (8.2 g), polyethylene oxide (5.5 g), water (217 g), and a ammonium hydroxide solution (2.5 wt. %, 16 g) is prepared. This mixture is added to a Thermo Haake Rheomix 3000 mixer (625 mL internal volume) and mixed using sigma shaped blades. The blades are turned in a counter-rotating fashion at 50 rpm by a Thermo Haake Rheocord 300p drive unit over a 30 min period to produce a well mixed paste. The paste is aged in a sealed plastic bag for 24 h. The paste is then extruded into ⅛" cylinders using a Thermo Haake Rheomex 202p with a Rheocord 300p drive unit. The extrudates are dried at room temperature for 24 h, and then at 105° C. for 16 h. The extrudates are calcined at 700° C. using the temperature ramp of 1° C./min from room temperature to 500° C., held at 500° C. for 1 h and then ramped from 500° C. to 700° C. at 10° C./min and held at 700° C. for 6 h.

The calcined titania extrudates (24 g) are added to a 250-mL round bottom flask containing a mixture of DIUF water (101 g), aqueous $Na_2PdCl_4$ solution (20.3 wt. % Pd, 0.65 g), and 0.6358 gm of aqueous $NaAuCl_4$ solution (20 wt. % Au, 0.63 g). $NaHCO_3$ powder is added to the mixture until the pH reaches 7.14. A total of 1.7 g $NaHCO_3$ is added, which causes bubbling as $CO_2$ is generated. The flask is placed on the rotovap at 40° C. and rotated at 35 rpm for 4 h. The solid is filtered and washed with DIUF water (150 g). The solid obtained is dried at 60° C. for 24 h in a nitrogen-purged oven, then at 60° C. for 3 h in a vacuum oven. It is then calcined in air at 300° C. for 4 h. The calcined material is extracted with DIUF water in a Soxhlet extractor for 24 h to wash out residual chloride. It is dried in air, then dried under vacuum at 60° C., and finally calcined in air at 550° C. for 4 h. The calcined material is reduced in a nitrogen/hydrogen (95/5) atmosphere at 100° C. in a down flow quartz tube for 8 h. The final catalyst (Catalyst I) contains 0.33% Pd and 0.31% Au. Its surface area is 26 $m^2/g$.

COMPARATIVE EXAMPLES 15-17

Propylene Epoxidation with a Mixture of TS-1 Extrudate and Pd/Au-On-Titania Extrudate The procedure of Example 8 is repeated, except a mixture of Catalyst H and Catalyst I is used instead of Catalyst C. The amounts of catalysts used and epoxidation results are shown in Table 2.

In Table 2, mixtures of TS-1-containing particles (about 1 mm in diameter) and supported noble metal particles (about 1 mm in diameter) are used as catalysts. The results show that the catalyst productivity is very low and the productivity is not affected by the catalyst loading. In contrast, catalysts in Table 1 with similar particle size (about 1 mm), which are formed from TS-1 crystals with mean mass diameter of 0.2 μm and supported noble metals with mean mass diameter of 1.4 μm, give much higher productivities (comparing Example 8 and Example 15).

TABLE 1

Propylene Epoxidation with Composite Catalysts

| | Example | | | | |
|---|---|---|---|---|---|
| | 8 | 9 | 10 | 11 | 12 |
| Catalyst | C | D | E | F | G |
| Catalyst Type | extrudate | extrudate | extrudate | extrudate | pellet |
| Amount (g) | 15 | 25 | 20 | 40 | 20 |
| Binder | silica | alumina | alumina | alumina | alumina |
| Pd wt. % | 0.08 | 0.07 | 0.05 | 0.06 | 0.07 |
| Au wt. % | 0.03 | 0.03 | 0.04 | 0.04 | 0.17 |
| Ti wt. % | 5.7 | 6.4 | 7.1 | 8.2 | 8.6 |
| Al wt. % | N/A* | 18 | 13 | 11 | 4.4 |
| Mean mass diameter of catalyst (mm) | 1 | 1 | 1 | 1 | 1 |
| Surface area ($m^2/g$) | 320 | 320 | N/A* | N/A* | N/A* |
| Amount of Pd contained (mg) | 12.0 | 17.5 | 10.0 | 24.0 | 14.0 |
| Amount of Au contained (mg) | 4.5 | 7.5 | 8.0 | 16.0 | 340 |
| Mean mass diameter of zeolite (μm) | 0.2 | 0.2 | 0.2 | 0.2 | 0.2 |
| Mean mass diameter of supported noble metal (μm) | 1.4 | 1.4 | 1.4 | 1.4 | 1.4 |
| Epoxidation | | | | | |
| Catalyst productivity (g POE/g Cat/h) | 0.13 | 0.07 | 0.08 | 0.04 | 0.08 |
| PO/POE selectivity (%) | 84 | 73 | 73 | 70 | 60 |
| Propylene to POE selectivity (%) | 85 | 80 | 80 | 65 | 89 |

*N/A = Not Analyzed.

TABLE 2

Propylene Epoxidation with Mixed Catalysts

| | Example | | |
|---|---|---|---|
| | C. 15 | C. 16 | C. 17 |
| TS-1 Catalyst | | | |
| Catalyst | H | H | H |
| Amount of Catalyst (g) | 11.0 | 21.0 | 25.0 |
| Ti wt. % | 1.4 | 1.4 | 1.4 |
| Amount of TS-1 contained (g) | 8.47 | 16.17 | 20 |
| Mean mass diameter (mm) | 1 | 1 | 1 |
| Noble Metal Catalyst | | | |
| Catalyst | I | I | I |
| Amount of Catalyst (g) | 1.5 | 5.0 | 10.0 |
| Pd wt % | 0.33 | 0.33 | 0.33 |

TABLE 2-continued

Propylene Epoxidation with Mixed Catalysts

| | Example | | |
|---|---|---|---|
| | C. 15 | C. 16 | C. 17 |
| Au wt % | 0.31 | 0.31 | 0.31 |
| Amount of Pd contained (mg) | 5.0 | 16.5 | 33.0 |
| Amount of Au contained (mg) | 4.6 | 15.5 | 31.0 |
| Mean mass diameter (mm) | 1 | 1 | 1 |
| Epoxidation | | | |
| Catalyst productivity (g POE/g Cat/h) | 0.033 | 0.027 | 0.037 |
| PO/POE selectivity (%) | 82 | 76 | 70 |
| Propylene to POE selectivity (%) | 79 | 72 | 87 |

We claim:

1. A catalyst comprising a transition metal zeolite and a supported noble metal, wherein the mean mass diameter of the catalyst is greater than 0.5 mm, and wherein the catalyst is formed from transition metal zeolite particles and the supported noble metal particles each having a mean mass diameter of less than 0.1 mm.

2. The catalyst of claim 1 wherein the transition metal zeolite particles and the supported noble metal particles each has a mean mass diameter of smaller than 0.05 mm.

3. The catalyst of claim 1 wherein the transition metal zeolite particles and the supported noble metal particles each has a mean mass diameter of smaller than 0.02 mm.

4. The catalyst of claim 1 wherein the transition metal zeolite is a titanium zeolite.

5. The catalyst of claim 1 wherein the transition metal zeolite is TS-1.

6. The catalyst of claim 1 wherein the noble metal is selected from the group consisting of gold, silver, platinum, palladium, iridium, ruthenium, rhenium, rhodium, osmium, and mixtures thereof.

7. The catalyst of claim 1 wherein the noble metal is palladium, gold, or a palladium-gold mixture.

8. The catalyst of claim 1 wherein the noble metal is supported on a carrier selected from the group consisting of silicas, aluminas, titanias, and mixtures thereof.

9. The catalyst of claim 8 wherein the carrier is a titania.

10. An epoxidation process comprising reacting an olefin, hydrogen, and oxygen in the presence of the catalyst of claim 1.

11. The process of claim 10 wherein the catalyst is in a fixed bed.

12. The process of claim 10 wherein the transition metal zeolite is TS-1.

13. The process of claim 10 wherein the noble metal is selected from the group consisting of gold, silver, platinum, palladium, iridium, ruthenium, rhenium, rhodium, osmium, and mixtures thereof.

14. The process of claim 10 wherein the noble metal is palladium, gold, or a palladium-gold mixture.

15. The process of claim 10 wherein the noble metal is supported on a carrier selected from the group consisting of silicas, aluminas, titanias, and mixtures thereof.

16. The process of claim 15 wherein the carrier is a titania.

17. The process of claim 16 wherein the noble metal is a palladium-gold mixture.

18. The process of claim 10 performed in a solvent.

19. The process of claim 18 performed in the presence of a buffer.

20. The process of claim 10 wherein the olefin is propylene.

* * * * *